United States Patent
Bourne et al.

(10) Patent No.: US 9,731,065 B2
(45) Date of Patent: Aug. 15, 2017

(54) DEVICES, SYSTEMS, AND METHODS FOR TIP VACUUM CONTROL DURING ASPIRATION

(71) Applicant: Novartis AG, Basel (CH)

(72) Inventors: John Morgan Bourne, Irvine, CA (US); John Richard Carpenter, Irvine, CA (US)

(73) Assignee: Novartis AG, Basel (CH)

( * ) Notice: Subject to any disclaimer, the term of this patent is extended or adjusted under 35 U.S.C. 154(b) by 648 days.

(21) Appl. No.: 14/097,316

(22) Filed: Dec. 5, 2013

(65) Prior Publication Data

US 2015/0157501 A1  Jun. 11, 2015

(51) Int. Cl.
*A61M 3/02* (2006.01)
*A61F 9/007* (2006.01)
*A61M 1/00* (2006.01)

(52) U.S. Cl.
CPC ....... *A61M 3/0283* (2013.01); *A61F 9/00736* (2013.01); *A61F 9/00745* (2013.01);
(Continued)

(58) Field of Classification Search
CPC .............. A61M 1/0031; A61M 1/0023; A61M 1/0084; A61M 1/0039; A61M 1/008; A61M 1/0041; A61M 1/0058; A61M 1/3672; A61M 2210/0612; A61M 3/0283; A61F 9/00745; A61F 9/00736; A61F 9/00763

See application file for complete search history.

(56) References Cited

U.S. PATENT DOCUMENTS 3,469,582 A * 9/1969 Jackson .............. A61M 1/0043
  137/510
4,182,385 A  1/1980 Williamson
(Continued)

FOREIGN PATENT DOCUMENTS

EP  1117358  3/2008
EP  2273958  8/2014
(Continued)

OTHER PUBLICATIONS

International Search Report and Written Opinion issued for PCT/US2014/064416 dated Feb. 18, 2015, 11 pgs.
(Continued)

*Primary Examiner* — Theodore Stigell
*Assistant Examiner* — Benjamin Koo

(57) ABSTRACT

Disclosed herein is an apparatus for insertion in an eye of a patient for aspirating material from the eye in the treatment of an ocular condition, the apparatus comprising a needle disposed at a distal end of the apparatus, an aspiration channel extending from a distal aperture of the needle to a proximal end of the apparatus, and an irrigation sleeve coaxially disposed about the needle. The aspiration channel comprises a proximal portion having a first diameter, a bypass portion having a second diameter and at least one bypass port, and a distal portion having a third diameter. The second diameter is larger than the first diameter. The irrigation sleeve and the needle form an annular irrigation passageway therebetween. The bypass port is shaped and configured to establish fluid communication between the irrigation passageway and the aspiration channel.

3 Claims, 8 Drawing Sheets

(52) U.S. Cl.
CPC ......... *A61M 1/0031* (2013.01); *A61M 1/0084* (2013.01); *A61M 2210/0612* (2013.01)

(56) References Cited

U.S. PATENT DOCUMENTS

| | | | |
|---|---|---|---|
| 4,516,398 | A | 5/1985 | Wuchinich |
| 4,808,154 | A | 2/1989 | Freeman |
| 5,188,589 | A | 2/1993 | Wypych et al. |
| 5,282,786 | A | 2/1994 | Ureche |
| 5,354,265 | A | 10/1994 | Mackool |
| 5,417,654 | A | 5/1995 | Kelman |
| 5,484,398 | A | 1/1996 | Stoddard |
| 5,505,693 | A | 4/1996 | Mackool |
| 5,634,912 | A | 6/1997 | Injev |
| 5,645,530 | A | 7/1997 | Boukhny et al. |
| 5,674,226 | A | 10/1997 | Doherty et al. |
| 5,725,495 | A * | 3/1998 | Strukel ............... A61M 1/0035 604/22 |
| 6,013,046 | A | 1/2000 | Maaskamp et al. |
| 6,033,376 | A | 3/2000 | Rockley |
| 6,050,971 | A | 4/2000 | Garnier et al. |
| 6,340,355 | B1 | 1/2002 | Barrett |
| 6,361,520 | B1 | 3/2002 | Rockley |
| 6,398,754 | B1 | 6/2002 | Sutton et al. |
| 6,605,054 | B2 * | 8/2003 | Rockley ............. A61F 9/00745 604/22 |
| 7,014,629 | B2 | 3/2006 | Mackool |
| 7,094,229 | B2 | 8/2006 | Boukhny et al. |
| 7,276,060 | B2 | 10/2007 | Madden |
| 7,967,775 | B2 | 6/2011 | Hong |
| 8,267,891 | B2 | 9/2012 | Dimalanta et al. |
| 8,423,126 | B2 | 4/2013 | Mackool |
| 8,579,929 | B2 | 11/2013 | Mackool et al. |
| 2003/0078591 | A1 * | 4/2003 | Barrett ............... A61M 1/0031 606/107 |
| 2005/0277897 | A1 | 12/2005 | Ghannoum et al. |
| 2006/0047241 | A1 | 3/2006 | Boukhny |
| 2006/0229632 | A1 | 10/2006 | Madden et al. |
| 2006/0264995 | A1 * | 11/2006 | Fanton ............. A61B 17/32002 606/180 |
| 2007/0260173 | A1 | 11/2007 | Boukhny et al. |
| 2011/0319810 | A1 | 12/2011 | Ghannoum |
| 2012/0157934 | A1 | 6/2012 | Liao et al. |
| 2014/0052053 | A1 | 2/2014 | Hong et al. |
| 2014/0163454 | A1 | 6/2014 | Sussman et al. |
| 2014/0257172 | A1 | 9/2014 | Yalamanchili |
| 2015/0112356 | A1 | 4/2015 | Chon et al. |
| 2015/0157501 | A1 | 6/2015 | Bourne et al. |
| 2015/0157502 | A1 | 6/2015 | Velasco et al. |

FOREIGN PATENT DOCUMENTS

| | | |
|---|---|---|
| WO | WO 95/24865 | 9/1995 |
| WO | WO 00/74615 | 12/2000 |
| WO | WO 2009/138049 | 11/2009 |

OTHER PUBLICATIONS

Georgescu et al., "Objective Measurement of Postocclusion Surge During Phacoemulsification in Human Eye-Bank Eyes," American Journal of Ophthalmology, vol. 143, No. 3, pp. 437-440, 440 el (2007) (5 pages).

Payne et al., "Phacoemulsification tip vacuum pressure: Comparison of 4 devices," J Cataract Refract Surg, vol. 32, pp. 1375-1377, (2006).

* cited by examiner

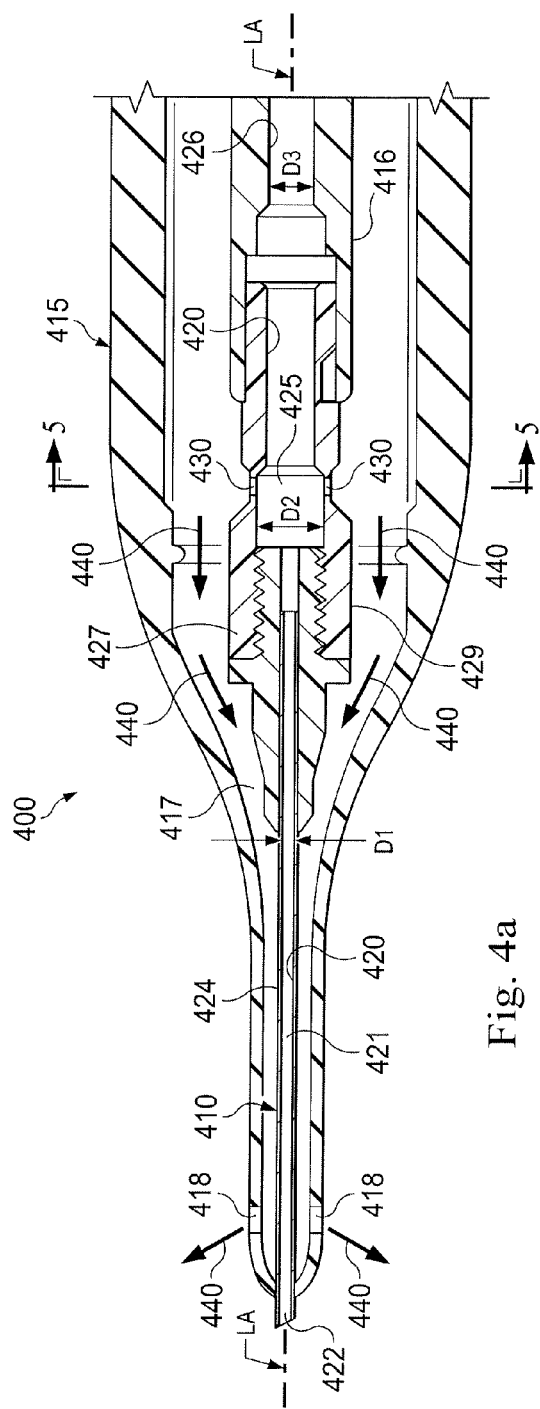
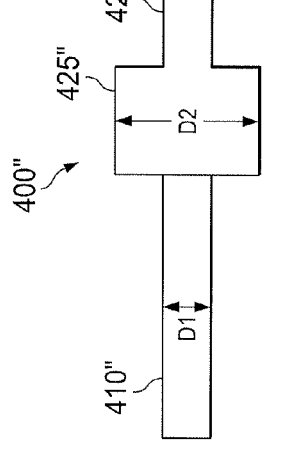
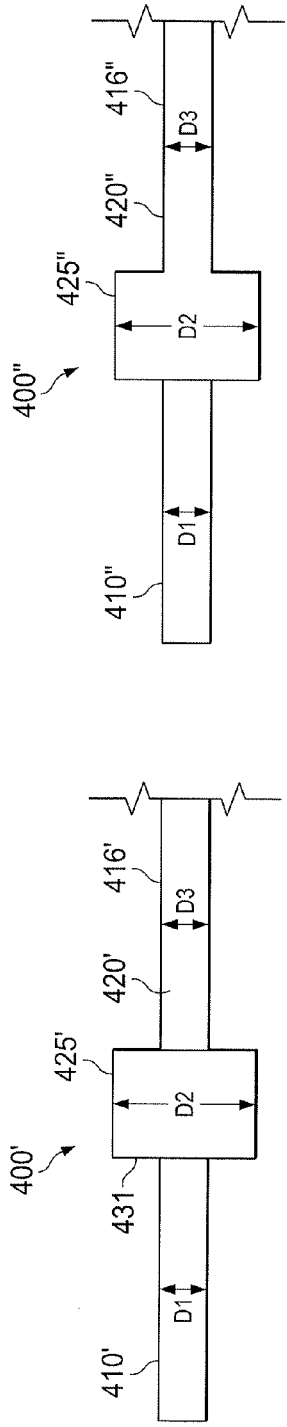
Fig. 4a
Fig. 4b
Fig. 4c

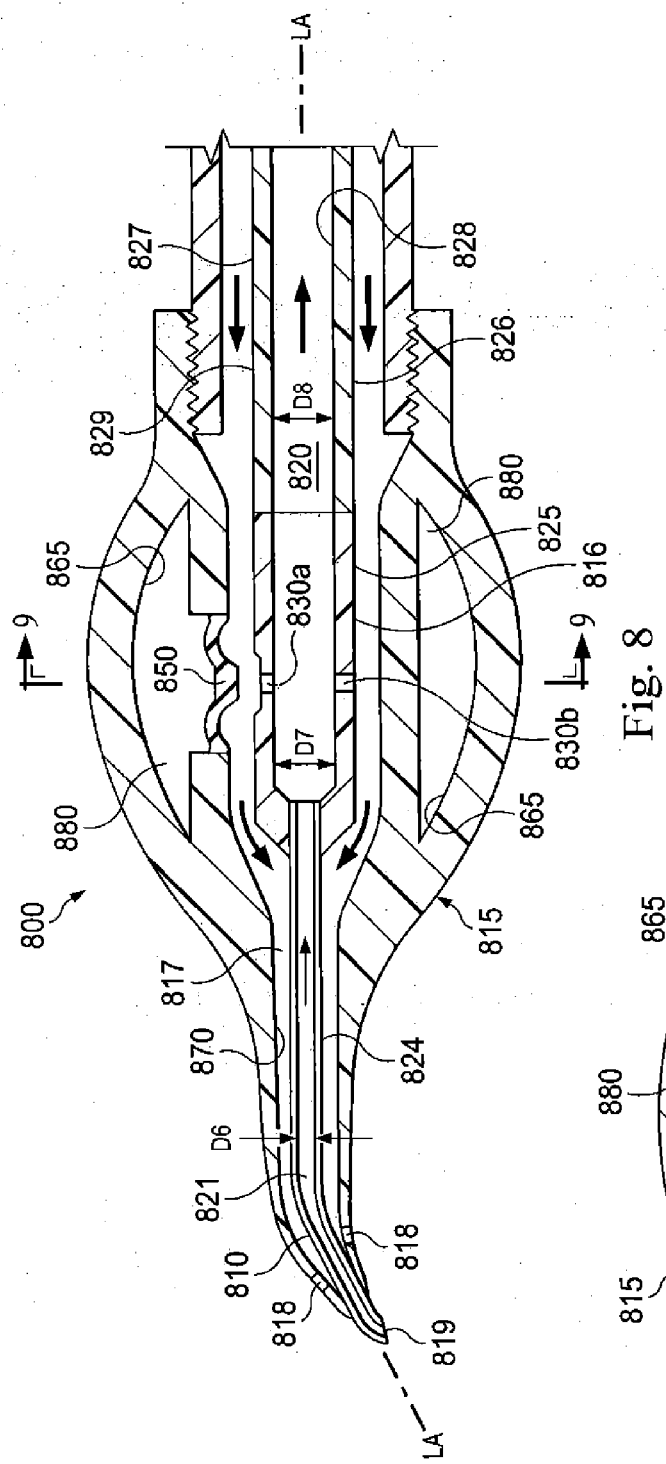
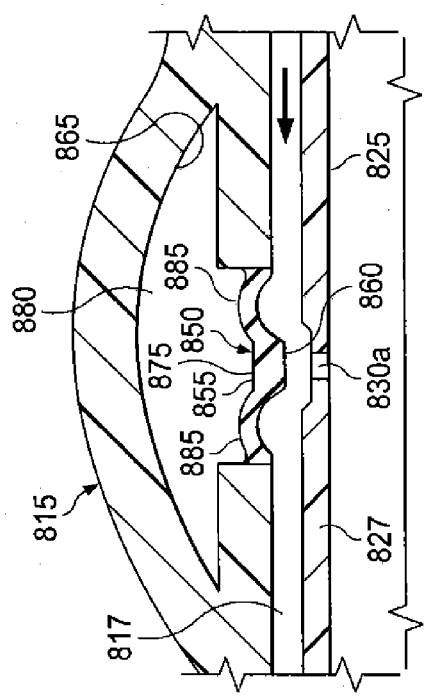

DEVICES, SYSTEMS, AND METHODS FOR TIP VACUUM CONTROL DURING ASPIRATION

BACKGROUND

Visually impairing cataract, or clouding of the lens, is the leading cause of preventable blindness in the world. An accepted treatment for cataracts is surgical removal of the affected lens and replacement with an artificial intraocular lens ("IOL"). Cataract extractions are among the most commonly performed operations in the world.

FIG. 1 is a diagram of an eye 10 showing some of the anatomical structures related to the surgical removal of cataracts and the implantation of IOLs. The eye 10 comprises a lens 12, an optically clear cornea 14, and an iris 16. A lens capsule 18, located behind the iris 16 of the eye 10, contains the lens 12, which is seated between an anterior capsule segment or anterior capsule 20 and a posterior capsular segment or posterior capsule 22. The anterior capsule 20 and the posterior capsule 22 meet at an equatorial region of the lens capsule 18. The eye 10 also comprises an anterior chamber 24 located in front of the iris 16 and a posterior chamber 26 located between the iris 16 and the lens capsule 18.

The eye 10 functions to provide vision by transmitting light through the cornea 14, and focusing the image by way of the lens 10 onto a retina 25. The quality of the focused image depends on many factors including the size and shape of the eye, and the transparency of the cornea 14 and the lens 10. When age or disease causes the lens to become less transparent or opacified, vision deteriorates because of the diminished light which may be transmitted to the retina 25. The cataract is this deficiency in the lens 10.

A common technique of cataract surgery known as extracapsular cataract extraction ("ECCE") involves the creation of an incision 30 near the outer edge of the cornea 14 and an opening in the anterior capsule 20 (i.e., an anterior capsulotomy) through which the opacified lens 12 is removed. The lens 12 can be removed by various known methods including phacoemulsification, in which ultrasonic energy is applied to the lens 12 to break it into small pieces that are promptly aspirated from the lens capsule 18.

A common complication of phacoemulsification procedures arises from a blockage or occlusion of the aspirating needle. As the irrigation fluid and emulsified tissue is aspirated away from the interior of the eye through the hollow cutting needle, pieces of emulsified tissue may become at least momentarily lodged in the aspirating lumen. Such blockages may cause undesirable pressure changes in the eye and/or the handpiece. For example, when the aspiration lumen is clogged, vacuum pressure may rapidly increase within the lumen. After the clog is removed, the resulting drop in anterior chamber pressure is known as post-occlusion surge, which can cause a large quantity of fluid and tissue to be aspirated out of the eye too quickly, potentially causing the eye to collapse and/or causing the lens capsule 18 to be torn.

Various equipment designs and methods have been derived in order to minimize the problems introduced by a blocked aspiration lumen during a phacoemulsification procedure or other cataract removal procedure. However, there remains a need for devices, systems, and methods to more effectively prevent or minimize these blockages. The devices, systems, and methods disclosed herein overcome one or more of the deficiencies of the prior art.

SUMMARY

In one exemplary aspect, the present disclosure is directed to an apparatus for insertion in an eye of a patient for aspirating material from the eye in the treatment of an ocular condition. In one aspect, the apparatus comprises a needle disposed at a distal end of the apparatus with an aspiration channel extending from the distal aperture of the needle to a proximal end of the apparatus. In one aspect, the aspiration channel comprises a proximal portion having a first diameter, a bypass portion having a second diameter, and a distal portion having a third diameter, wherein the second diameter is larger than the first diameter. In one aspect, the apparatus includes an irrigation sleeve coaxially disposed about the needle, with the irrigation sleeve and the needle forming an annular irrigation passageway therebetween. In one aspect, the apparatus includes at least one bypass port formed within the bypass portion of the aspiration channel. In one aspect, the at least one bypass port is shaped and configured to establish fluid communication between the irrigation passageway and the aspiration channel.

In another exemplary aspect, the present disclosure is directed to an apparatus for insertion in an eye of a patient for aspirating material from the eye in the treatment of an ocular condition. In one aspect, the apparatus comprises an aspiration channel extending from a distal end to a proximal end of the apparatus. In one aspect, the aspiration channel comprises a proximal portion having a first diameter, a bypass portion having a second diameter, and a distal portion having a third diameter. In one aspect, the distal portion is in fluid communication with the distal aperture of the needle. In one aspect, the second diameter is larger than the first diameter. In one aspect, the apparatus comprises an irrigation sleeve coaxially disposed about the aspiration channel, with the irrigation sleeve and the aspiration channel forming an annular irrigation passageway therebetween. In one aspect, the apparatus comprises at least one bypass port formed within the bypass portion of the aspiration channel, wherein the at least one bypass port is shaped and configured to establish fluid communication between the irrigation passageway and the aspiration channel. In one aspect, the apparatus comprises a sealing element disposed on the irrigation sleeve adjacent the irrigation passageway, with the sealing element being shaped and configured to selectively seat against the at least one bypass port and block fluid flow through the at least one bypass port with the application of force on the sealing element.

In another exemplary aspect, the present disclosure is directed to a method for controlling vacuum pressures within an aspiration handpiece for insertion within an eye of a patient. In one aspect, the method includes positioning a distal tip of the aspiration handpiece within the eye, with the distal tip in fluid communication with an aspiration channel extending from the distal tip to a proximal end of the handpiece. In one aspect, the aspiration channel includes a distal portion having a first diameter and a bypass portion having a second diameter that is larger than the first diameter and including at least one bypass port. In one aspect, the method includes providing irrigation fluid to the eye through an irrigation sleeve coaxially disposed about the aspiration channel, with the irrigation sleeve and the needle forming an annular irrigation passageway therebetween. In one aspect, the method includes allowing irrigation fluid to pass from the irrigation passageway into the aspiration lumen through the at least one bypass port. In one aspect, the method includes providing a vacuum pressure within the aspiration channel to aspirate fluid and tissue from the eye through the distal tip into the aspiration channel.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

FIG. 4a illustrates a partially cross-sectional view of a distal portion of an exemplary instrument according to one embodiment consistent with the principles of the present disclosure.

FIG. 4b illustrates a diagram of a distal portion of an exemplary instrument according to one embodiment consistent with the principles of the present disclosure.

FIG. 4c illustrates a diagram of an exemplary instrument according to one embodiment consistent with the principles of the present disclosure.

FIG. 8 illustrates a cross-sectional view of an exemplary instrument according to another embodiment consistent with the principles of the present disclosure.

FIG. 10 illustrates a detailed view of the exemplary bypass portion shown in FIG. 8 where the bypass port is in an open condition according to one embodiment consistent with the principles of the present disclosure.

DETAILED DESCRIPTION

Figure 1:
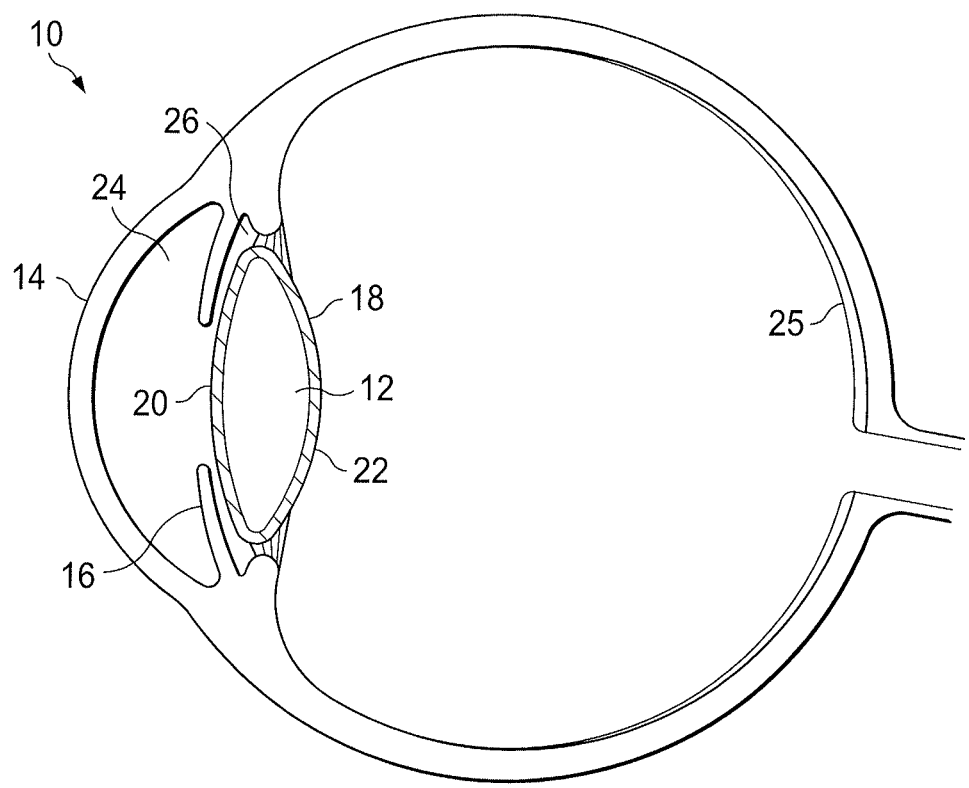
FIG. 1 is a diagram of a cross-sectional view of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The present disclosure relates generally to devices, systems, and methods for use in treating medical conditions, including ophthalmic conditions such as cataract. In some instances, embodiments of the present disclosure comprise surgical instruments designed to reduce the occurrence of blockages of the aspiration lumen of a surgical handpiece during cataract extraction and minimizing the negative effects of such blockages. In some exemplary embodiments disclosed herein, the instrument includes at least one bypass port disposed within an area of increased inner diameter along the aspiration path. Having the bypass ports disposed within an area of increased diameter along the path of aspiration of the instrument may reduce the risk of occluding a bypass port, which consequently reduces the risk of post-occlusion surge. In some exemplary embodiments disclosed herein, the surgical instrument is configured to allow the user to selectively affect the vacuum level within the handpiece by temporarily blocking at least one bypass port with the aspiration path by manually manipulating an irrigation sleeve surrounding the aspiration path. The embodiments disclosed herein allow the user to actively control the aspiration vacuum at the tip of the instrument by manipulating the irrigation sleeve at a specific aspiration flow rate to either (1) reduce the bypass surface area and immediately increase the tip vacuum, or (2) revert to the original bypass surface area to immediately decrease the tip vacuum.

Figure 2:
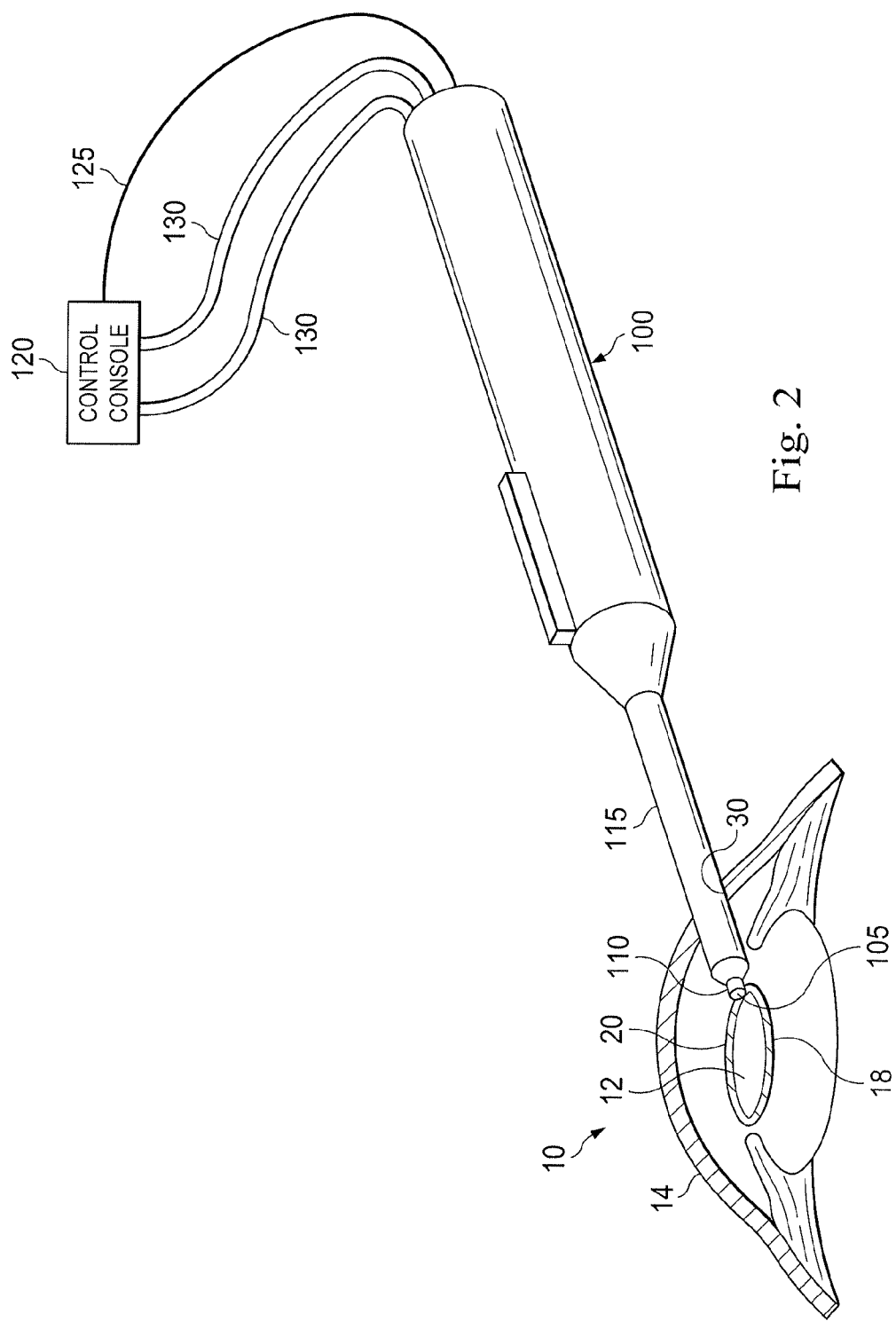
FIG. 2 illustrates a perspective view of an exemplary instrument positioned within the eye according to one embodiment consistent with the principles of the present disclosure.

FIG. 2 illustrates a common technique of cataract surgery known as extracapsular cataract extraction ("ECCE"), which involves the creation of an incision 30 near the outer edge of the cornea 14 and an opening in the anterior capsule 20 (i.e., an anterior capsulotomy) through which the opacified lens 12 is removed. The lens 12 can be removed by various known methods including phacoemulsification, in which ultrasonic energy is applied to the lens 12 to break it into small pieces that are promptly aspirated from the lens capsule 18.

FIG. 2 depicts an aspiration instrument 100 for removing the lens 12 by emulsification and aspiration through the incision 30 in accordance with the present disclosure. The instrument 100 may be any of a variety of handpieces configured for aspiration of material from the interior of the eye 10, including, by way of non-limiting example, a phacoemulsification handpiece. A typical surgical handpiece suitable for phacoemulsification procedures consists of an ultrasonically driven phacoemulsification handpiece, an attached hollow cutting needle surrounded by an irrigating sleeve, and an electronic control console. The instrument 100 includes an aspiration tip 105, a hollow cutting needle 110, and an irrigation sleeve 115. The irrigation sleeve 115 surrounds the cutting needle 110 and is disposed co-axially about a longitudinal axis of the cutting needle 110. The instrument 100 may be attached to a control console 120 by an electric cable 125 and flexible tubing 130. Through the electric cable 125, the console 120 may vary the power level transmitted by the instrument 100 to the cutting needle 110. In some embodiments, the control console 120 includes a display, a guided user interface, and/or other accessory devices (not shown). The flexible tubing 130 supplies irrigation fluid to the surgical site through the irrigation sleeve 115 and draws aspiration fluid from the eye 10 through aspiration tip 105 of the instrument 100.

During the phacoemulsification procedure, the aspiration tip 105 of the cutting needle 110 and the end of the irrigation sleeve 115 are inserted into the anterior capsule 20 through the incision near the outer edge of the cornea 14. The surgeon brings the cutting needle 110 into contact with the lens 12 so that the vibrating tip emulsifies or fragments the lens. By way of non-limiting example, various forms of energy that may be coupled to the cutting needle 110 include ultrasonic energy, laser energy, thermal energy, and electrical energy. The resulting fragments are aspirated out of the eye 10 through an interior lumen 135 (not shown in FIG. 2) of the cutting needle 110 along with the irrigation solution provided to the eye 10 during the procedure. Following removal of the opacified lens 12, an artificial IOL is typically implanted within the lens capsule 18 through the opening in the anterior capsule 20 to mimic the transparency and refractive function of a healthy lens.

Figure 3:
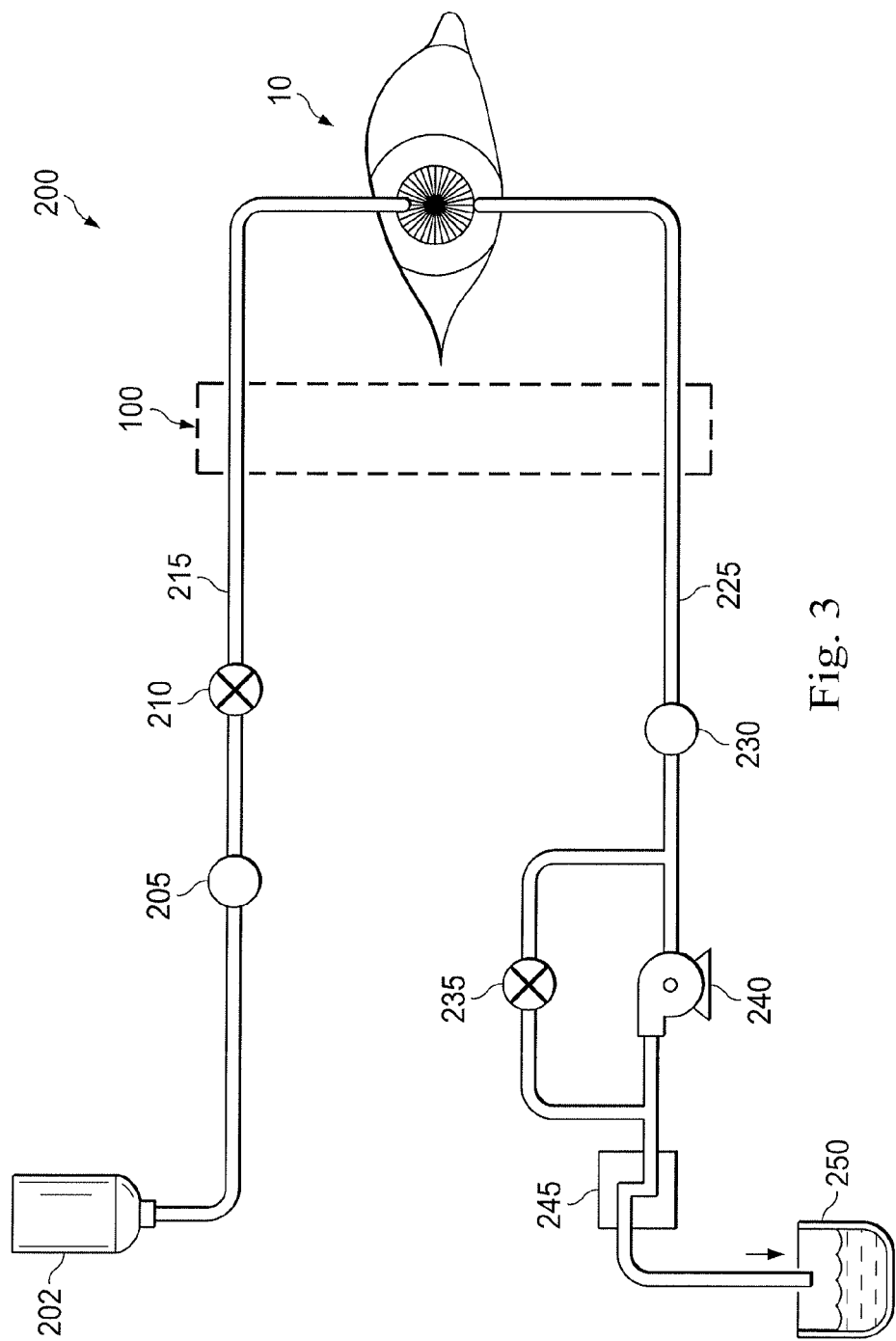
FIG. 3 is a diagram of the components in the fluid path of an exemplary phacoemulsification system according to one embodiment consistent with the principles of the present disclosure.

FIG. 3 is a diagram of the components in the fluid path of an exemplary phacoemulsification system 200 according to one embodiment consistent with the principles of the present disclosure. FIG. 3 depicts the fluid path through the eye 10 during a phacoemulsification procedure. The components include an irrigation fluid source 202, an irrigation pressure sensor 205, an irrigation valve 210, an irrigation line 215, the instrument 100, an aspiration line 225, an aspiration pressure sensor 230, a vent valve or bypass port 235, a pump 240, a reservoir 245, and a drain bag 250. In some embodiments, the irrigation line 215 and the aspiration line 225 may be the same as the flexible tubing 130 described above in relation to FIG. 2. The irrigation line 215 provides irrigation fluid to the eye 10 during the procedure. The pump 240 operates to draw fluid and emulsified tissue (e.g., lens tissue) from the eye and through the aspiration line 225 during the procedure. The aspiration pressure sensor 230 measures the vacuum pressure within the aspiration line 225, and may be able to detect an increase in vacuum pressure associated with an occlusion inside the aspiration line 225 (and/or a decrease in vacuum pressure associated with occlusion break). The aspirated fluid and tissue passes through the reservoir 245 into the drain bag 250.

Some embodiments actively monitor sensed data from the aspiration pressure sensor and actively adjust the operation of the instrument 100 (e.g., the vacuum level of the pump 240 and/or the flow rate) in response to the sensed aspiration pressure. Some embodiments may lack an aspiration pressure sensor 230. Some embodiments may lack active pressure measurement monitoring altogether. Various instruments 100 may be capable of producing vacuum pressures of over 700 mm Hg in milliseconds. However, very high vacuum pressures may be undesirable in certain surgical applications, including, by way of non-limiting example, capsule polishing and cortex removal. In such embodiments, the aspiration vacuum levels may need to be controlled via adjusting the flow rate to mitigate potential risks associated with sharply elevated pressures within the aspiration line 225. In some embodiments, the instrument 100 may utilize the vent valve 235 to vent or relieve the vacuum pressure within the aspiration line 225 created by the pump 240.

When the irrigation fluid exits the irrigation fluid source 202, the fluid travels through the irrigation line 215 and into the eye 10. The irrigation pressure sensor 205 measures the pressure of the irrigation fluid in the irrigation line 215, and may be capable of detecting an increase in pressure associated with an occlusion within the aspiration line 225 (and/or a decrease in vacuum pressure associated with occlusion break). The irrigation pressure sensor 205 may comprise any of a variety of fluid pressure sensors and may be located anywhere in the irrigation fluid path (i.e., anywhere between the irrigation fluid source 202 and the eye 10). The irrigation valve 210 may provide on/off control of the irrigation. Other embodiments may lack an irrigation pressure sensor 205 and/or an irrigation valve 210.

FIG. 4a illustrates a distal portion of a handpiece 400, which may be the same as the instrument 100 described above with reference to FIGS. 2 and 3. The handpiece 400 includes a cutting needle 410, an irrigation sleeve 415, and a body 416. The cutting needle 410 and the irrigation sleeve 415 may be the same as the cutting needle 110 and the irrigation sleeve 115 described above with relation to FIGS. 2 and 3. As mentioned above in relation to FIG. 2, the handpiece 400 is placed in the eye 10 during a cataract removal procedure, such as, by way of non-limiting example, a phacoemulsification procedure. In some embodiments, the cutting needle 410 may be ultrasonically vibrated to break up or emulsify the diseased lens. The irrigation fluid flows from the irrigation line 215 through the irrigation passageway 416 to exit into the eye through the irrigation ports 418 in the direction of arrows 440.

The irrigation sleeve 415 concentrically surrounds the cutting needle 410 to define an annular irrigation passageway 417 therebetween. The irrigation sleeve 415 includes at least one irrigation port 418 disposed near a distal tip or distal aperture 422 of the cutting needle 410. For example, in the pictured embodiment, the irrigation sleeve 415 includes two irrigation ports 418.

In the pictured embodiment, the irrigation sleeve 415 is detachably coupled to the cutting needle 410. The irrigation sleeve 415 may be detachably coupled to the cutting needle 410 by any of a variety of means, including, by way of non-limiting example, a threaded engagement, a snap-fit engagement, a frictional engagement, and/or any other mechanism for temporarily connecting the irrigation sleeve 415 to the handpiece 400. The cutting needle 410 may be likewise coupled to the body 418 of the handpiece 400 by any of a variety of detachable or temporary means, including, by way of non-limiting example, a threaded engagement, a snap-fit engagement, a frictional engagement, and/or any other mechanism for temporarily connecting the cutting needle 410 to the handpiece 400.

An aspiration channel 420 extends through the cutting needle 410 and the body 416 along a longitudinal axis LA of the handpiece 400. The aspiration channel 420 defines an aspiration lumen 421 running therethough, which may be fluidically coupled to the aspiration line 225 to enable deposition of aspirated material into the reservoir 245 and/or the drain bag 250 (described above in relation to FIG. 3). A distal tip 422 of the cutting needle 410 comprises an opening in fluid communication with the aspiration lumen 421. Fluid and emulsified tissue may be aspirated from the eye through the distal tip 422 into the aspiration lumen 421 of the cutting needle 410.

In the pictured embodiment, the aspiration channel 420 includes a distal portion 424, a bypass portion 425, and a proximal portion 426. The bypass portion 425 is shaped and configured as a passageway between the distal portion 424 and the proximal portion 426 of the aspiration channel 420. The proximal portion runs through the body 416 of the handpiece 400, and the distal portion 424 runs through the cutting needle 410.

The bypass portion 425 may be formed as part of the cutting needle 410, as a separate coupler or attachment, or as part of the body 416 of the handpiece 400. In the pictured embodiment in FIG. 4a, the bypass portion forms a proximal extension of the cutting needle 410. In other embodiments, as shown in FIG. 4b, the bypass portion 425' of an aspiration lumen 420' of an instrument 400' may comprise a separate coupler 431 that can be removably coupled to the body 416' and the cutting needle 410'. In other embodiments, as shown in FIG. 4c, the bypass portion 425" of an aspiration lumen 420" of an instrument 400" may form a distal extension of the body 416" coupled to a needle 410".

The aspiration channel 420 extends through various component parts of the handpiece 400, and includes an inner or luminal diameter that varies along the length of the aspiration channel 420. The inner diameter varies between the distal portion 424, the bypass portion 425, and the proximal portion 426. The distal portion 424 includes an inner diameter D1, the bypass portion 425 includes an inner diameter D2, and the proximal portion includes an inner diameter D3. In the pictured embodiment, the inner diameter D2 of the bypass portion 425 is greater than the inner diameter D1 of the distal portion 424 and the inner diameter D3 of the proximal portion 426. In some other embodiments, the inner diameter D2 of the bypass portion 425 may be substantially the same as the inner diameter D3 of the proximal portion 426.

Figure 5:
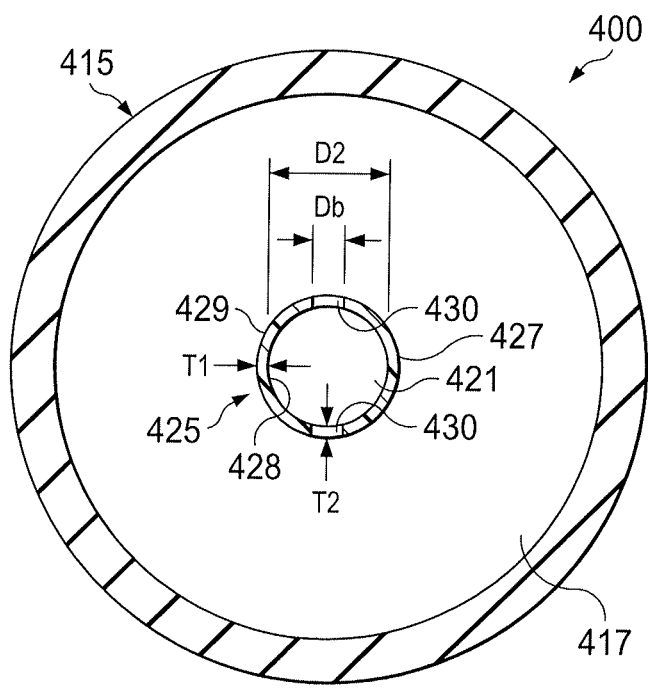
FIG. 5 illustrates a cross-sectional view of the instrument shown in FIG. 4a along lines 5-5 in the area of an exemplary bypass portion according to one embodiment consistent with the principles of the present disclosure.

FIG. 5 illustrates a cross-sectional view of the instrument 400 along line 5-5 in FIG. 4a at the bypass portion 425. As shown in FIG. 5, the bypass portion 425 comprises a housing 427 having an inner surface 428 and an outer surface 429. The inner surface 428 is in contact with the aspirated fluid and tissue material within the aspiration lumen 421 of the aspiration channel 420. The outer surface 429 is in contact with the irrigation passageway 417. The housing 427 includes a wall thickness T1 extending from the inner surface 428 to the outer surface 429. In some embodiments, the thickness T1 is constant throughout the entire bypass portion 425. In other embodiments, the thickness T1 varies either longitudinally along the length of the bypass portion 425 or at discrete areas such as adjacent a bypass port 430, which is described below with reference to FIGS. 4 and 5.

As shown in FIGS. 4 and 5, the bypass portion 425 includes at least one bypass port 430. The bypass port 430 is an aperture in the housing 427 of the bypass portion 425 that fluidically connects the aspiration lumen 421 with the irrigation passageway 417 in the area of the bypass portion 425. The bypass port 430 includes a sidewall thickness T2, which may be substantially the same as the wall thickness T1 of the bypass portion 425. In other embodiments, the thickness T2 of the sidewall of the bypass port 430 may be less than the thickness of the remainder of the housing 427 of the bypass portion. In some embodiments, as described further below with reference to FIGS. 6-11, the user may control the vacuum pressure within the aspiration channel 420 by selectively opening and closing the bypass port to 430 selectively decrease and increase, respectively, the vacuum pressure while maintaining a substantially constant aspiration flow rate.

As shown in FIG. 5, the bypass ports 430 include an inner diameter Db that spans the width of the apertures in the housing 427. In some embodiments, the diameter Db ranges from 0.005-0.020 inches. For example, in one embodiment, the diameter Db may measure 0.006 in. These measurements are provided by way of example only, and are not intended to be limiting. Other diameters are contemplated. Although the bypass ports 430 in the pictured embodiment have a circular shape, the bypass ports 430 may be formed in any of a variety of shapes, including without limitation, ovoid, rectangular, crescent, slit-like, and rhomboid shapes.

In the pictured embodiment, the bypass portion 425 includes two bypass ports 430. It should be understood that a varying number of bypass ports 430 can be used and that the bypass ports 430 may be arranged on the bypass portion 425 in any of a variety of patterns. For example, such bypass ports 430 can be staggered with respect to each other rather than being formed directly opposite one another. The bypass ports 430 may be positioned at the same or different longitudinal positions along the length of the bypass portion 425. For example, at least one bypass port 430 may be disposed farther from the distal tip 422 of the cutting needle 410 than at least one other bypass port 430.

As mentioned above, very high vacuum pressures may be undesirable in certain surgical applications, including, by way of non-limiting example, capsule polishing and cortex removal. In such surgical applications, the instrument 100 may utilize the bypass port 430 (in combination with relatively low aspiration rates) to relieve the vacuum pressure within the aspiration line 225 created by the pump 240 and to maintain the vacuum levels at the desired low level. Bypass ports in traditional aspiration lines may be occluded by aspirated tissue as it travels past the bypass port within the aspiration channel, which results in a rapid increase in vacuum pressure within the aspiration channel. In contrast, the bypass ports 430 described herein are disposed within the bypass portion 425, which is an area of increased inner diameter along the aspiration channel 420. By increasing the inner diameter of the portion of the aspiration channel 420 (i.e., the bypass portion 425) carrying the bypass ports 430 relative to the remainder of the aspiration channel 420, the risk of occlusion is minimized. In particular, the relatively large inner diameter D2 of the bypass portion 425 reduces the risk of inadvertent occlusion of the bypass ports 430 with aspirated material. This, in turn, reduces the risk of unintended and/or uncontrolled rises in vacuum levels during aspiration. In addition, at low flow rates and higher bypass volumes or cross-sectional areas, the tip vacuum level will decrease significantly upon the occurrence of a tip occlusion. In applications involving polishing of the lens capsule, for example, this provides added protection to the lens capsule because the propensity of the tip for inadvertently "grabbing" the capsule is reduced. Thus, having the bypass ports 430 disposed within the larger bypass portion 425 allows the user more control over vacuum pressure variations in surgical instruments that traditionally exhibited extremely rapid changes in vacuum levels within the aspiration channel 420 during unintentional occlusion of bypass ports.

The aspiration channels 420 and, in particular, the bypass portions 425 described herein can be made from a variety of suitable materials without departing from the scope of the present disclosure. By way of non-limiting example, the instrument tips described herein can be made from titanium, stainless steel, alloys thereof, or any other suitable material.

Figure 6:
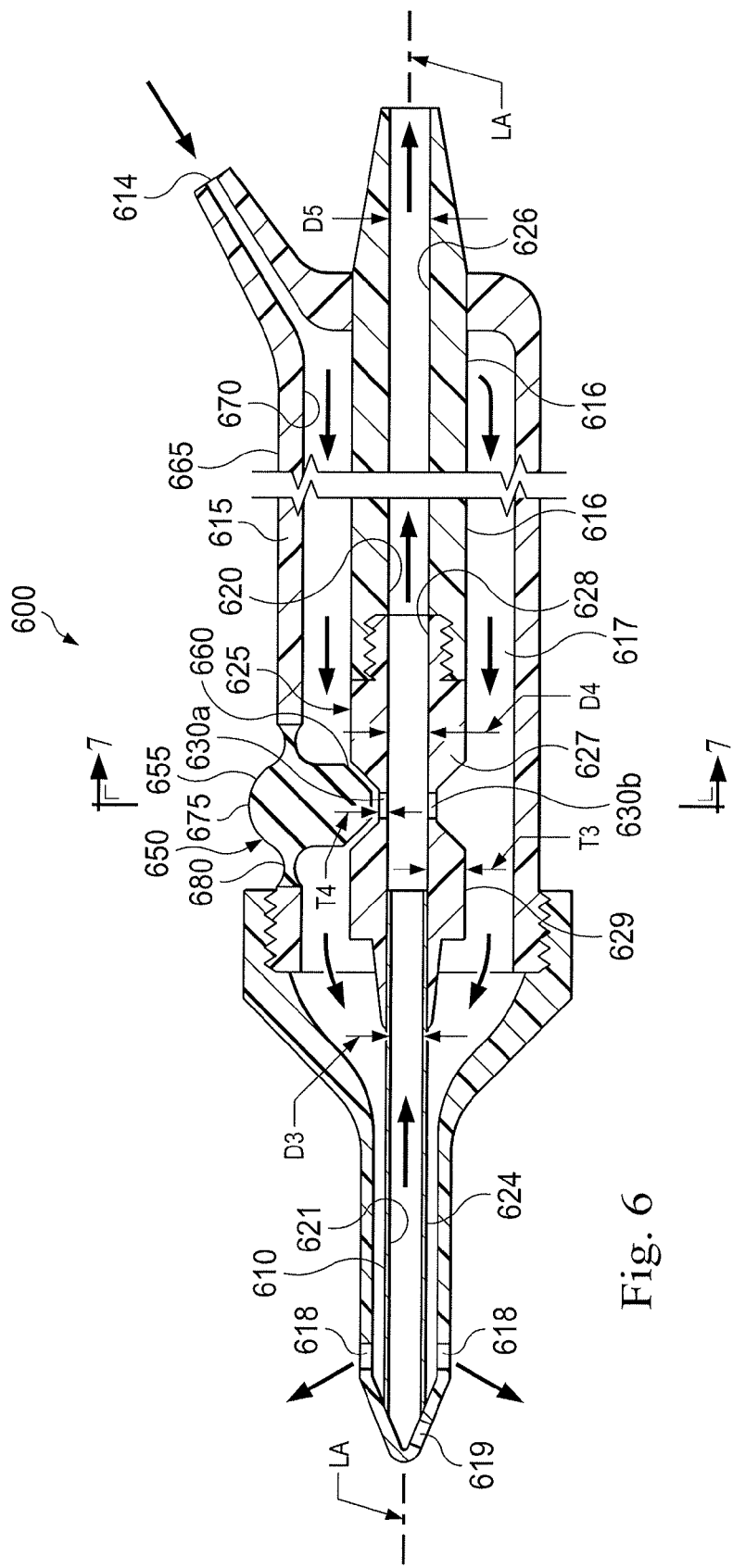
FIG. 6 illustrates a cross-sectional view of an exemplary instrument according to another embodiment consistent with the principles of the present disclosure.

FIG. 6 illustrates a cross-sectional view of an exemplary handpiece 600 according to another embodiment consistent with the principles of the present disclosure. In some embodiments, the handpiece 600 may be the same as the instrument 100 described above with reference to FIGS. 2 and 3. The handpiece 600 includes a cutting needle 610, an irrigation sleeve 615, and a body 616. The cutting needle 610 and the irrigation sleeve 615 may be the same as the cutting needle 110 and the irrigation sleeve 115 described above with relation to FIGS. 2 and 3.

The irrigation sleeve 615 concentrically surrounds the cutting needle 610 to define an annular irrigation passageway 617 therebetween. The irrigation sleeve 615 includes at least one inlet port 614 shaped and configured to allow the influx of irrigation solution into the irrigation passageway 617. The irrigation sleeve 615 includes at least one irrigation port 618 disposed near a distal tip 619 of the cutting needle 610. For example, in the pictured embodiment, the irrigation sleeve 615 includes two irrigation ports 618. The irrigation ports 618 are shaped and configured to allow the efflux of irrigation fluid into the eye during surgical procedure. The irrigation sleeve includes a sealing element 650 that is shaped and configured to selectively contact and seal against the bypass port 630. The sealing element 650 is described in further detail below with reference to FIGS. 6 and 7.

In the pictured embodiment, the irrigation sleeve 615 is detachably coupled to the cutting needle 610. The irrigation sleeve 615 may be detachably coupled to the cutting needle 610 be any of a variety of means, including, by way of non-limiting example, a threaded engagement, a snap-fit engagement, a frictional engagement, and/or any other mechanism for temporarily connecting the irrigation sleeve 615 to the handpiece 600. The cutting needle 610 may be likewise coupled to the body 618 of the handpiece 600 by any of a variety of detachable or temporary means, including, by way of non-limiting example, a threaded engagement, a snap-fit engagement, a frictional engagement, and/or any other mechanism for temporarily connecting the cutting needle 610 to the handpiece 600.

An aspiration channel 620 extends through the cutting needle 610 and the body 616 along a longitudinal axis LA of the handpiece 600. The aspiration channel 620 defines an aspiration lumen 821 running therethough, which may be fluidically coupled to the aspiration line 225 to enable deposition of aspirated material into the reservoir 245 and/or the drain bag 250 (described above in relation to FIG. 3). The distal tip 619 of the cutting needle 610 comprises an opening in fluid communication with the aspiration lumen 621. The aspiration channel 620 extends through various component parts of the handpiece 600, and may include an inner or luminal diameter that varies along the length of the aspiration channel 620.

In the pictured embodiment, the aspiration channel 620 includes a distal portion 624, a bypass portion 625, and a proximal portion 626. The bypass portion 625 is shaped and configured as a passageway between the distal portion 624 and the proximal portion 626 of the aspiration channel 620. The proximal portion 626 runs through the body 616 of the handpiece 400, and the distal portion 624 runs through the cutting needle 610. The bypass portion 625 may be formed as part of the cutting needle 610, as a separate coupler or attachment, or as part of the body 616 of the handpiece 600. In the pictured embodiment, the bypass portion forms a proximal extension of the cutting needle 610. In other embodiments, the bypass portion 625 may comprise a separate coupler that can be removably coupled to the body 616 and the cutting needle 610. In other embodiments, the bypass portion 625 may form a distal extension of the body 616.

In some embodiments, the bypass portion 625 is substantially similar to the bypass portion 425 described above in relation to FIGS. 4 and 5, except for the differences described herein. The inner diameter may vary between the distal portion 624, the bypass portion 625, and the proximal portion 626 as described in relation to the handpiece 400. In other embodiments, an inner diameter D4 of the bypass portion 625 may be substantially the same as an inner diameter D3 of the distal portion 624 and/or an inner diameter D5 of the proximal portion 626. For example, in the pictured embodiment in FIG. 6, the inner diameter D4 of the bypass portion 625 is larger than the inner diameter D3 of the distal portion 624, but is substantially the same as the inner diameter D5 of the proximal portion 626.

As shown in FIG. 6, the bypass portion 625 comprises a housing 627 having an inner surface 628 and an outer surface 629. The inner surface 628 is in contact with the aspirated fluid and tissue material within the aspiration lumen 621 of the aspiration channel 620. The outer surface 629 is in contact with the irrigation passageway 617.

Figure 7:
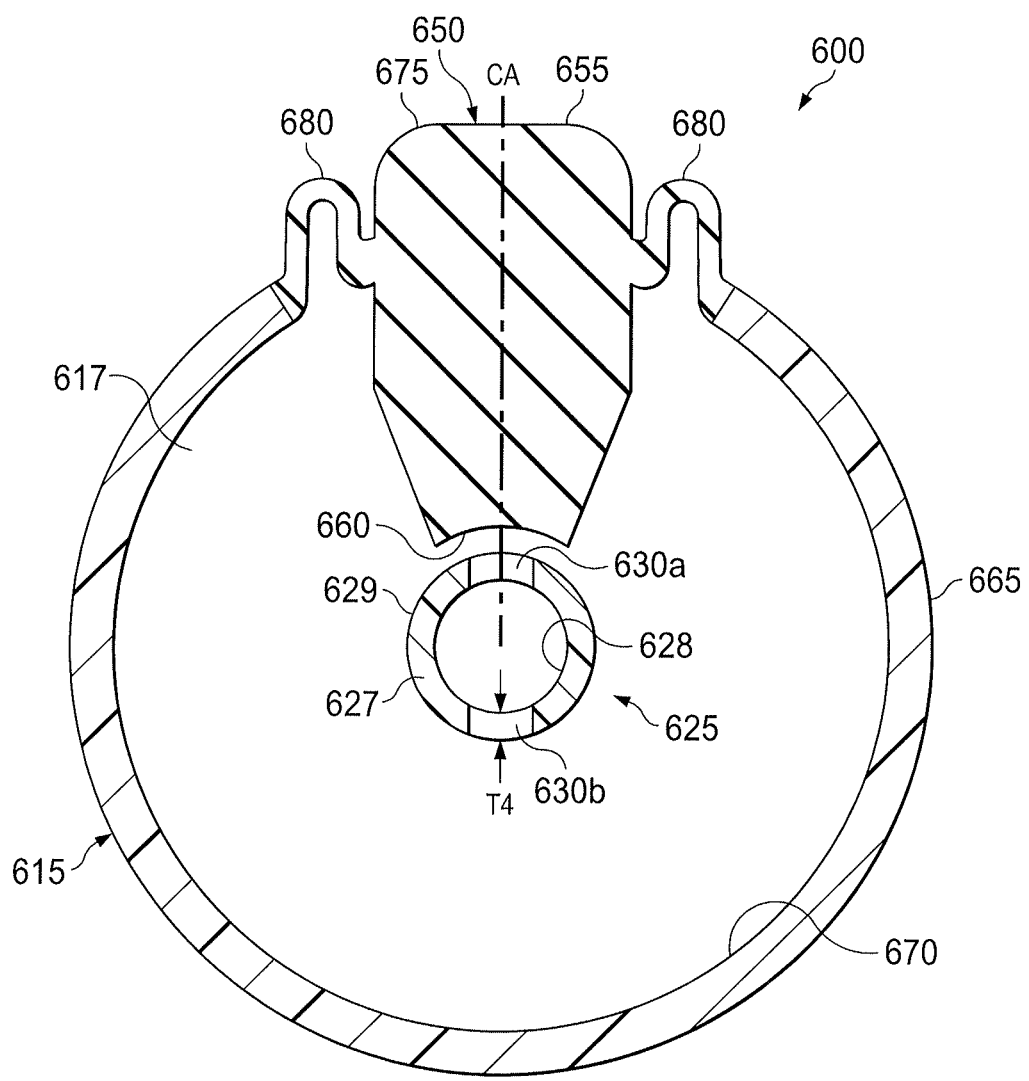
FIG. 7 illustrates a cross-sectional view of an exemplary bypass portion of the instrument shown in FIG. 6 according to one embodiment consistent with the principles of the present disclosure.

FIG. 7 illustrates a cross-sectional view of the bypass portion 625 along the line 7-7 according to one embodiment consistent with the principles of the present disclosure. As shown in FIGS. 6 and 7, the bypass portion 625 includes at least one bypass port 630. In the pictured embodiment, the bypass portion 625 includes two bypass ports, 630a and 630b. Other embodiments may include only the bypass port 630a. In the pictured embodiment, the bypass ports 630a and 630b are disposed opposite each other at a substantially identical longitudinal distance along the aspiration channel 620 from the distal tip 619. In the pictured embodiment, the bypass ports 630a and 630b are sized identically. In other embodiments, the bypass port 630a may be sized to have a larger cross-sectional area than the bypass port 630b, thereby allowing for a greater reduction in flow rate when the bypass port 630a is blocked to increase tip vacuum.

It should be understood that a varying number of bypass ports 630 can be used and that the bypass ports 630 may be arranged on the bypass portion 625 in any of a variety of patterns. For example, the bypass ports 630a, 630b can be staggered with respect to each other rather than being formed directly opposite one another as shown. The bypass ports 630a, 630b may be positioned at the same or different longitudinal positions along the length of the bypass portion 625. For example, the bypass port 630a may be disposed farther from the distal tip 619 of the cutting needle 610 than the bypass port 630b. Although the bypass ports 630a, 630b in the pictured embodiment have a circular shape, the bypass ports 630a, 630b may be formed in any of a variety of shapes, including without limitation, ovoid, rectangular, crescent, slit-like, and rhomboid shapes.

The housing 627 includes a wall thickness T3 extending from the inner surface 628 to the outer surface 629. In some embodiments, the thickness T3 varies either longitudinally along the length of the bypass portion 625 or at discrete areas such as adjacent a bypass port 630. For example, in the pictured embodiment, the housing 627 is shaped to receive at least a portion of the sealing element 650 and the thickness T3 decreases in the area adjacent the bypass ports 630a, 630b to accommodate the sealing element 650. In other embodiments, the thickness T3 is constant throughout the entire bypass portion 625.

The bypass ports 630a, 630b are apertures in the housing 627 of the bypass portion 625 that fluidically connect the aspiration lumen 621 with the irrigation passageway 617 in the area of the bypass portion 625. As shown in FIGS. 6 and 7, the bypass ports 630a, 630b include a sidewall thickness T4, which is less than the thickness T3 of the housing 627 in other areas of the bypass portion 625. In other embodiments, the thickness T4 of the sidewall of the bypass ports 630a, 630b may be substantially the same as the wall thickness T3 of the bypass portion 625.

As mentioned above, the irrigation sleeve 615 includes the sealing element 650, which is disposed on the irrigation sleeve 615 so as to overlie at least one of the bypass ports 630. As shown in FIG. 7, the sealing element 650 is disposed on the irrigation sleeve 615 such that the sealing element 650 and the bypass port 630a are coaxially aligned about a central axis CA extending through the bypass port 630a. In the pictured embodiment in FIGS. 6 and 7, the sealing element 650 comprises a pushbutton-like structure that may be depressed onto the bypass port 630a to reduce or eliminate flow through the bypass port 630a.

The sealing element 650 includes an exterior side 655 and an opposing interior side 660. The exterior side 655 is substantially continuous with an exterior surface 665 of the irrigation sleeve 615. The exterior side 655 is shaped and configured to facilitate a user's manual depression of the sealing element 650. The interior side 660 is substantially continuous with an interior surface 670 of the irrigation sleeve 615. The interior side 660 is shaped and configured to block flow through the bypass port 630a when the sealing element 650 is depressed inward to contact the outer surface 629 of the housing 627 of the bypass portion 625. In some embodiments, the interior side 660 may be deformable and shape under pressure to seat at least partially within the bypass port 630a.

The sealing element 650 includes a central section 675 and a peripheral section 680, which circumferentially surrounds the central section 675. When the sealing element 650 is depressed, the central section 675 moves toward the housing 627 of the bypass portion 625. When the interior side 660 of the sealing element 650 contacts the outer surface 629 of the housing 627, the sealing element 650 blocks the ingress and/or egress of fluid and tissue through the bypass port 630a. The sealing element 650 contacts the irrigation sleeve 615 at the peripheral section 680. In the pictured embodiment, the central section 675 is substantially thicker than the peripheral section 680. In the pictured embodiment, the peripheral section 680 is curved to facilitate the inward and outward movement of the sealing element 650. In other embodiments, the peripheral section 680 is substantially flat.

In some embodiments, the sealing element 650 may be formed as an integral part of the irrigation sleeve 615. In other embodiments, the sealing element 650 may be formed as a separate component of the handpiece 600 that is fixedly attached the irrigation sleeve 615 by the peripheral section 680 by welding, overmolding, adhesive, or any other suitable means for fixedly attaching the sealing element 650 to the irrigation sleeve 615 in a fluid-tight fashion.

In some embodiments, the sealing element 650 is formed of silicone. In other embodiments, the sealing element 650 may be constructed of any of a variety of suitable materials, including by way of non-limiting example, silicon, nitrile rubber, and polyisoprene.

It should be understood that a varying number of sealing elements 650 can be used to correspond to the number of bypass ports 630 in the handpiece 600. For example, other embodiments may include another sealing element 650b (not shown) on the irrigation sleeve 615 shaped and configured to block flow through the bypass port 630b. The bypass ports 630 and their corresponding sealing elements 650 may be arranged relative to the bypass portion 625 in any of a variety of patterns. As mentioned above, some embodiments may lack bypass port 630b.

The aspiration channels 620 and, in particular, the bypass portions 625 described herein can be made from a variety of suitable materials without departing from the scope of the present disclosure. By way of non-limiting example, the instrument tips described herein can be made from titanium, stainless steel, alloys thereof, or any other suitable material.

While using handpieces capable of producing a rapid increase in aspiration vacuum to 700 mmHg or more within a short time (e.g., 20 to 30 milliseconds), the user may control the vacuum pressure by utilizing the bypass ports (e.g., bypass ports 630a, 630b) and varying the overall aspiration flow rate. In general, the resulting tip vacuum pressure produced at a specific aspiration flow rate is highly repeatable and predictable. In some applications, however, very high vacuum pressures may be desirable for very brief periods of time, including, by way of non-limiting example, during an occlusion of the distal tip 619 of the aspiration channel 620 to clear the occlusion. In some applications, rapid increases in vacuum pressure may improve the purchase of lens material when the distal tip 619 contacts the lens material. A user employing the handpiece 600 may rapidly increase the tip vacuum pressure within the aspiration lumen 620 without necessarily changing the aspiration flow rate.

In particular, the user may rapidly increase the tip vacuum pressure within the aspiration lumen 620 by depressing the sealing element 650 until the sealing element 650 contacts the bypass port 630a to selectively modify the amount of bypass available in the system. In particular, when the interior side 660 of the central section 675 of the sealing element 650 contacts the outer surface 629 of the housing 627 overlying the bypass port 630a, the sealing element 650 blocks the flow through the bypass port 630a. When the sealing element 650 contacts the bypass port 630a, the vacuum pressure within the aspiration lumen 621 rapidly increases, which allows the user to grab and aspirate unwanted tissue material through the distal tip 619 into the aspiration lumen 621. By selectively blocking the bypass port 630a and decreasing the total cross-sectional area of the bypass ports, higher tip vacuums can be attained quickly in order to capture and aspirate unwanted tissue while the handpiece 600 operates at a constant aspiration flow rate.

When the user releases or reduces manual pressure on the sealing element 650, the sealing element 650 will lift away from the bypass port 630a and return to a resting or neutral position. When the bypass port 630a is unblocked, the tip vacuum will immediately decrease. Accordingly, if tissue (e.g., the lens capsule) is inadvertently "grabbed" by the distal tip 619, the user can immediately release or decrease pressure on the sealing element 650 to reduce the tip vacuum and release the tissue from the distal tip 619. Therefore, the handpiece 600 enables the user to temporarily create a high tip vacuum without necessarily changing the overall aspiration flow rate. This allows the tip vacuum at a specific flow rate to remain repeatable and predictable. In the alternative, the user may reduce the aspiration flow rate to reduce the tip vacuum and release the tissue from the distal tip 619. In addition, the handpiece 600 allows the user more real-time control over aspiration vacuum pressures during ophthalmic surgeries, for example in response to occlusions within the aspiration lumen 621.

In some embodiments, the handpiece 600 may be connected to a control console 120 (as shown in FIG. 2) having display capabilities. In such embodiments, the control console may be configured to display the range of tip vacuum pressures that is possible using the handpiece 600. For example, at a known aspiration flow rate, the control console 120 may display both the tip vacuum pressure possible when the sealing element 650 is blocking the bypass port 630a and the tip vacuum pressure possible when the sealing element 650 is not blocking the bypass port 630a. Thus, the maximum and minimum tip vacuum levels could be displayed on the control console 120 as a direct function of the aspiration flow rate. In some embodiments, the control console 120 may display the real-time tip vacuum pressure.

FIG. 8 illustrates a cross-sectional view of a distal portion of an exemplary handpiece 800 according to another embodiment consistent with the principles of the present disclosure. In some embodiments, the handpiece 800 may be the same as the instrument 100 described above with reference to FIGS. 2 and 3. The handpiece 800 includes a cutting needle 810, an irrigation sleeve 815, and a body 816. The cutting needle 810 and the irrigation sleeve 815 may be the same as the cutting needle 110 and the irrigation sleeve 115 described above with relation to FIGS. 2 and 3. The cutting needle 815, the body 816, and the irrigation sleeve 815 are substantially similar to the cutting needle 610 and the body 616 described above in relation to FIGS. 6 and 7 except for the differences described herein.

The irrigation sleeve 815 concentrically surrounds the cutting needle 810 to define an annular irrigation passageway 817 therebetween. The irrigation sleeve 815 includes at least one irrigation port 818 disposed near a distal tip 819 of the cutting needle 810. For example, in the pictured embodiment, the irrigation sleeve 815 includes two irrigation ports 818. The irrigation ports 818 are shaped and configured to allow the efflux of irrigation fluid into the eye during surgical procedure.

The irrigation sleeve 815 includes a fluid-tight chamber 880. The fluid-tight chamber 880 comprises an annular space formed entirely within the irrigation sleeve 815. In addition, the irrigation sleeve 815 includes a sealing element 850 that is shaped and configured to selectively contact and seal against a bypass port 830a. The sealing element 850, the bypass port 830a, and the chamber 880 are described in further detail below with reference to both FIGS. 8 and 9.

An aspiration channel 820 extends through the cutting needle 810 and the body 816 along a longitudinal axis LA of the handpiece 400. The aspiration channel 820 defines an aspiration lumen 821 running therethough, which may be fluidically coupled to the aspiration line 225 to enable deposition of aspirated material into the reservoir 245 and/or the drain bag 250 (described above in relation to FIG. 3). The distal tip 819 of the cutting needle 810 comprises an opening in fluid communication with the aspiration lumen 821. The aspiration channel 820 extends through various component parts of the handpiece 800, and may include an inner or luminal diameter that varies along the length of the aspiration channel 820.

In the pictured embodiment, the aspiration channel 820 includes a distal portion 824, a bypass portion 825, and a proximal portion 826. The bypass portion 825 is shaped and configured as a passageway between the distal portion 824 and the proximal portion 826 of the aspiration channel 820. The proximal portion 826 runs through the body 816 of the handpiece 800, and the distal portion 824 runs through the cutting needle 810. The bypass portion 825 may be formed as part of the cutting needle 810, as a separate coupler or attachment, or as part of the body 816 of the handpiece 400. In the pictured embodiment, the bypass portion forms distal extension of the body 816. In other embodiments, the bypass portion 825 may comprise a separate coupler that can be removably coupled to the body 816 and the cutting needle 810. In other embodiments, the bypass portion 825 may form a proximal extension of the cutting needle 810.

In some embodiments, the bypass portion 825 is substantially similar to the bypass portion 425 described above in relation to FIGS. 4 and 5, except for the differences described herein. The inner diameter may vary between the distal portion 824, the bypass portion 825, and the proximal portion 826 as described in relation to the handpiece 400. In other embodiments, an inner diameter D7 of the bypass portion 825 may be substantially the same as an inner diameter D6 of the distal portion 824 and/or an inner diameter D8 of the proximal portion 826. For example, in the pictured embodiment in FIG. 8, the inner diameter D7 of the bypass portion 825 is larger than the inner diameter D6 of the distal portion 824, but is substantially the same as the inner diameter D8 of the proximal portion 826.

As shown in FIG. 8, the bypass portion 825 comprises a housing 827 having an inner surface 828 and an outer surface 829. The inner surface 828 is in contact with the aspirated fluid and tissue material within the aspiration lumen 821 of the aspiration channel 820. The outer surface 829 is in contact with the irrigation passageway 817.

Figure 9:
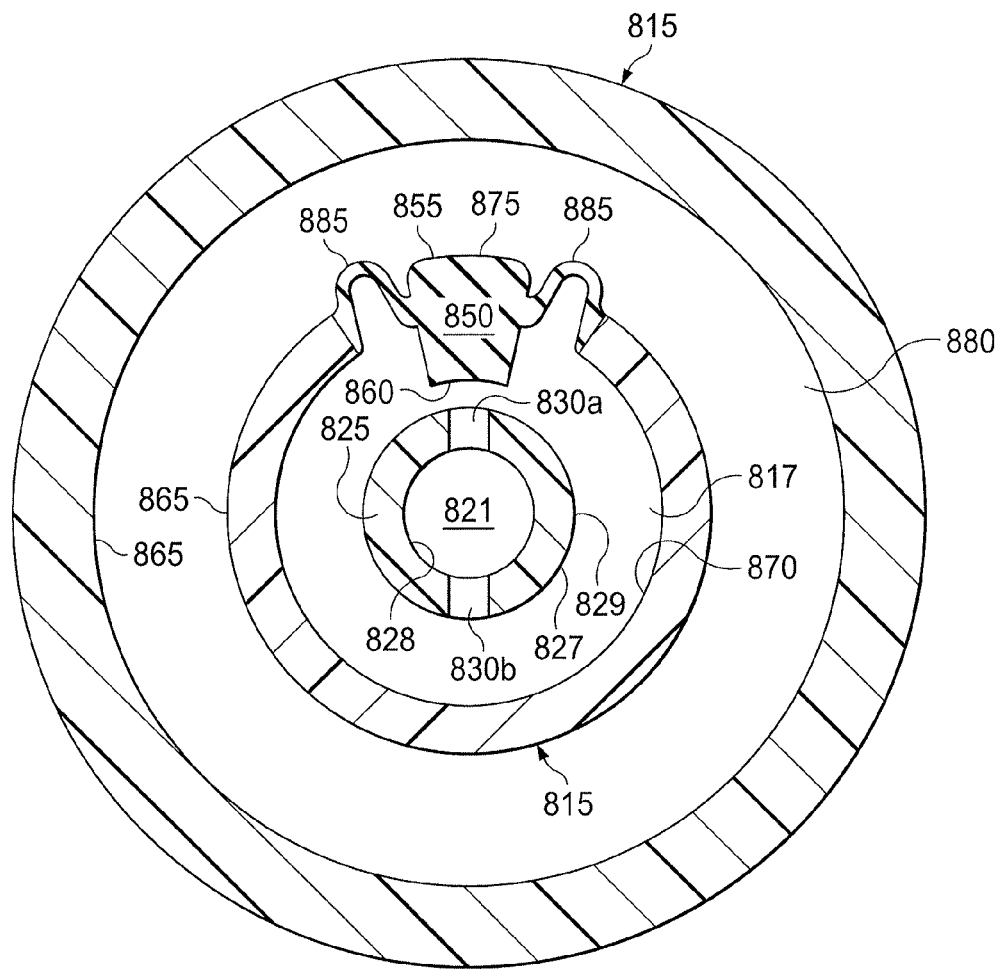
FIG. 9 illustrates a cross-sectional view of an exemplary bypass portion of the instrument shown in FIG. 8 according to one embodiment consistent with the principles of the present disclosure.

FIG. 9 illustrates a cross-sectional view of the bypass portion 825 along the line 9-9 according to one embodiment consistent with the principles of the present disclosure. The bypass portion 825 is substantially similar to the bypass portion 625 described above with relation to FIGS. 6 and 7 except for any differences described herein. As shown in FIGS. 8 and 9, the bypass portion 825 includes two bypass ports, 830a and 830b, which are disposed opposite each other at a substantially identical longitudinal distance along the aspiration channel 820 from the distal tip 819. The bypass ports 830a, 830b fluidically connect the aspiration lumen 821 with the irrigation passageway 817. It should be understood that a varying number of bypass ports 830 can be used and that the bypass ports 830 may be arranged on the bypass portion 825 in any of a variety of patterns.

As mentioned above, the irrigation sleeve 815 includes the chamber 880, which comprises an annular space disposed entirely within the irrigation sleeve 815. The irrigation sleeve 815 also includes the sealing element 850, which is disposed on the irrigation sleeve 815 between the chamber 880 and the irrigation passageway 817. As shown in FIG. 7, the sealing element 850 is disposed on the irrigation sleeve 815 such that the chamber 880, the sealing element 850, and the bypass port 830a are coaxially aligned about a central axis CA extending through the bypass port 830a. The chamber 880 may contain a predetermined volume of fluid, such a gas or a liquid. The chamber 880 is fluid-tight, so compression of the chamber 880 results in deformation of the chamber 880 and movement of the sealing element 850.

The sealing element 850 comprises a flexible, displaceable portion of the irrigation sleeve 815 that may shift onto the bypass port 830a to reduce or eliminate flow through the bypass port 830a. In the pictured embodiment in FIGS. 8 and 9, the sealing element 850 comprises an "M"-shaped, button-like structure. The sealing element 850 includes a first side 855 and an opposing second side 860. The first side 855 faces the chamber 880 and is substantially continuous with a chamber surface 865 of the irrigation sleeve 815. The second side 860 is substantially continuous with an interior surface 870 of the irrigation sleeve 815. The second side 860 is shaped and configured to block flow through the bypass port 830a when the sealing element 850 contacts the bypass port 830a. In particular, the second side 860 is shaped and configured to block flow through the bypass port 830a when the sealing element 850 is depressed inward to contact the outer surface 829 of the housing 827 of the bypass potion 825. In some embodiments, the second side 860 may deform under pressure to seat at least partially within the bypass port 830a.

As illustrated in FIGS. 8-11, the sealing element 850 includes a central section 875 and a peripheral section 885, which circumferentially surrounds the central section 875. As shown in detail in FIG. 10, the sealing element 850 contacts the irrigation sleeve 815 at the peripheral section 885. In the pictured embodiment, the central section 875 is substantially thicker than the peripheral section 885. The peripheral section 885 is curved to facilitate the inward and outward movement of the sealing element 850. In other embodiments, the peripheral section 885 is substantially flat. The sealing element 850 is shaped and configured to offer the area within the chamber 880 of least resistance to deformation.

Figure 11:
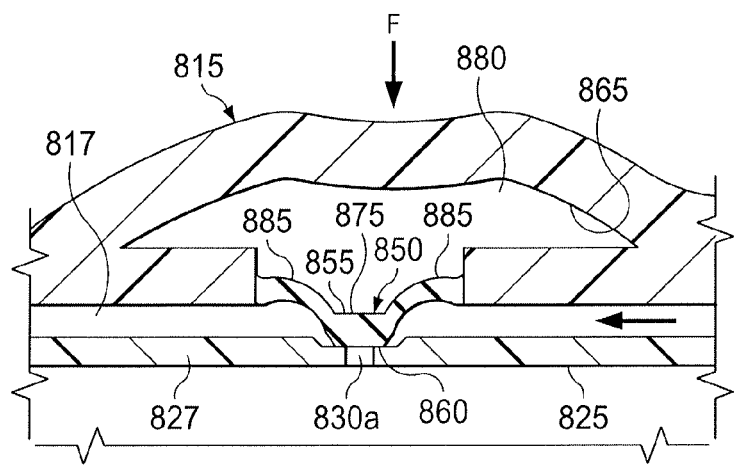
FIG. 11 illustrates a detailed view of the exemplary bypass portion shown in FIG. 8 where the bypass port is in a closed condition according to one embodiment consistent with the principles of the present disclosure.

Thus, as shown in FIG. 11, when the chamber 880 is compressed or force is applied to the irrigation sleeve 815 (e.g., by a user physically compressing the irrigation sleeve 815) and pressure increases within the chamber 880, the peripheral section 885 deforms and the central section 875 of the sealing element 850 moves toward the housing 827 of the bypass portion 825. It is important to note that the user may apply force on any portion of the irrigation sleeve 815 surrounding the annular chamber 880 in order to increase pressure within the chamber 880 and shift the sealing element 850 toward the bypass port 830a. Thus, in order to increase the aspiration vacuum within the aspiration lumen 821, the user need not position or reposition his or her hand to compress the area of the irrigation sleeve 815 overlying or adjacent to the sealing element 850. Instead, the user can simply apply pressure to the irrigation sleeve 815 anywhere surrounding the chamber 880. When the second side 860 of the sealing element 850 contacts the outer surface 829 of the housing 827, the sealing element 850 blocks the ingress and/or egress of fluid and tissue through the bypass port 830a. When the sealing element 850 blocks the bypass port 830a, the vacuum pressure within the aspiration lumen 821 rapidly increases.

In some embodiments, the sealing element 850 may be formed as an integral part of the irrigation sleeve 815. In other embodiments, the sealing element 850 may be formed as a separate component of the handpiece 800 that is fixedly attached to the irrigation sleeve 815 by the peripheral section 885 by welding, overmolding, adhesive, or any other suitable means for fixedly attaching the sealing element 850 to the irrigation sleeve 815 in a fluid-tight fashion. The irrigation sleeve 815 and/or the sealing element 850 may be formed of any of a variety of suitable flexible materials, including, by way of non-limiting example, silicon, nitrile rubber, and polyisoprene.

While using handpieces capable of producing a rapid increase in aspiration vacuum to 700 mmHg or more within a short time (e.g., 20 to 30 milliseconds), the user may control the vacuum pressure by utilizing the bypass ports (e.g., bypass ports 830a, 830b) and varying the overall aspiration flow rate. In general, the resulting tip vacuum pressure produced at a specific aspiration flow rate is highly repeatable and predictable. In some applications, however, very high vacuum pressures may be desirable for very brief periods of time, including, by way of non-limiting example, during an occlusion of the distal tip 819 of the aspiration channel 820 to clear the occlusion. In some applications, rapid increases in vacuum pressure may improve the purchase of lens material when the distal tip 819 contacts the lens material.

A user employing the handpiece 800 may rapidly increase the tip vacuum pressure within the aspiration lumen 820 without necessarily changing the aspiration flow rate. Because the chamber 880 is fluid-tight and extends circumferentially around the aspiration lumen 820, and because the sealing element 850 is the area of least resistance within the chamber 880, a user may compress any portion of the chamber 880 to increase the pressure within the chamber 880 and cause the sealing element 850 to shift and block the bypass port 830a. In particular, the user may compress the irrigation sleeve 815 anywhere around the circumference of the sleeve 815 in the area of the chamber 880 to increase pressure within the chamber 880 until the sealing element 850 contacts the bypass port 830a. This enables the user to block the bypass port 830a without necessarily reorienting the handpiece 800 or repositioning his grip of the handpiece 800. When the sealing element 850 contacts the bypass port 830a, the vacuum pressure within the aspiration lumen 821 rapidly increases. The handpiece 800 allows the user more real-time control over aspiration vacuum pressures during ophthalmic surgeries, for example in response to occlusions within the aspiration lumen 821.

By using the embodiments disclosed herein to control the bypass volume and flow rate, the vacuum at the tip can be actively controlled to achieve the very low tip vacuum levels required for certain ophthalmic applications (e.g., without limitation, capsule polishing), while also allowing the user to selectively increase the tip vacuum for tissue aspiration by depressing the sealing element 650, 850 (e.g., either directly as in handpiece 600 or by applying force to the silicone sleeve 815 in the handpiece 800). Depressing the sealing element 650, 850 onto the bypass port 630a, 830a, respectively, reduces the bypass volume at a specific flow rate and almost immediately increases the tip vacuum level. Releasing force on the sealing element 650, 850 allows flow to resume through the bypass port 630a, 830a and almost immediately decreases the tip vacuum level or restores the original tip vacuum level (e.g., as dictated by the control console 120).

Embodiments in accordance with the present disclosure provide users with an instrument having at least one bypass port in area of increased internal diameter within the aspiration channel, thereby reducing the risk of inadvertent increases in aspiration vacuum pressures secondary to blockage of the bypass port. Some embodiments provide users with an instrument that enables the user to selectively increase the vacuum within the aspiration tip/lumen (e.g., in order to capture and aspirate unwanted tissue) by depressing a button or sealing element to block at least one bypass port without adjusting the preset aspiration flow rate. Releasing the force applied to the button allows flow to resume through the bypass port(s), thus reducing the vacuum pressures within the aspiration lumen/tip. Some embodiments provide users with an instrument that enables the user to selectively increase the vacuum within the aspiration tip/lumen by compressing the irrigation sleeve to block at least one bypass port without adjusting the preset aspiration flow rate, reorienting the instrument, or reorienting the user's grip on the instrument. Releasing the force applied to the irrigation sleeve allows flow to resume through the bypass port(s), thus reducing the vacuum pressures within the aspiration lumen/tip.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure

We claim:

1. A method for controlling vacuum pressures within an aspiration handpiece for insertion within an eye of a patient, comprising:

positioning a distal tip of the aspiration handpiece within the eye, the distal tip in fluid communication with an aspiration channel extending from the distal tip to a proximal end of the handpiece, the aspiration channel including a distal portion having a first diameter and a bypass portion having a second diameter that is larger than the first diameter, the bypass portion including at least one bypass port;

providing irrigation fluid to the eye through an irrigation sleeve coaxially disposed about the aspiration channel, the irrigation sleeve and a needle forming an annular irrigation passageway therebetween;

allowing the irrigation fluid to pass from the irrigation passageway into the aspiration channel through the at least one bypass port; and providing a vacuum pressure within the aspiration channel to aspirate fluid and tissue from the eye through the distal tip into the aspiration channel;

increasing the vacuum pressure within the aspiration channel by selectively blocking flow through the at least one bypass port.

2. The method of claim 1, further comprising applying force on a sealing element disposed on the irrigation sleeve adjacent the irrigation passageway, the sealing element being shaped and configured to selectively seat against the at least one bypass port and block fluid flow through the at least one bypass port.

3. The method of claim 2, wherein applying force on a sealing element comprises compressing an annular chamber formed within the irrigation sleeve to circumferentially surround the aspiration channel, wherein the sealing element is disposed on the irrigation sleeve between the annular chamber and the irrigation passageway.

* * * * *